United States Patent [19]

Rinehart

[11] 4,213,915

[45] Jul. 22, 1980

[54] N-HALO-ALKYL THIOLCARBAMATES AND N-ALKENYL THIOLCARBAMATES

[75] Inventor: Jay K. Rinehart, Akron, Ohio

[73] Assignee: PPG Industries, Inc., Pittsburgh, Pa.

[21] Appl. No.: 701,384

[22] Filed: Jun. 30, 1976

[51] Int. Cl.[2] .................... C07C 155/08; A01N 9/12

[52] U.S. Cl. .................... 260/455 A; 424/300

[58] Field of Search .................... 260/455 A; 424/300

[56] References Cited

U.S. PATENT DOCUMENTS

| | | | |
|---|---|---|---|
| 2,863,899 | 12/1958 | Harris | 260/455 A |
| 2,901,498 | 8/1959 | Tilles et al. | 260/455 A |
| 2,977,209 | 3/1961 | Tilles et al. | 71/100 |
| 2,983,747 | 5/1961 | Campbell et al. | 260/455 A |
| 3,046,189 | 7/1962 | Jacobi et al. | 424/300 |
| 3,075,875 | 1/1963 | Margot | 424/300 |
| 3,161,666 | 12/1964 | Sowa | 260/455 A |
| 3,265,563 | 8/1966 | Tilles et al. | 424/300 |
| 3,301,885 | 1/1967 | Richter et al. | 260/455 A |
| 3,687,653 | 8/1972 | Bollinger et al. | 71/94 |
| 3,836,524 | 9/1974 | Pitt | 260/455 A |
| 3,846,467 | 11/1974 | Kudamatsu et al. | 260/455 A |
| 3,932,632 | 1/1976 | Adolphi et al. | 424/213 |

FOREIGN PATENT DOCUMENTS

| | | |
|---|---|---|
| 789575 | 7/1968 | Canada . |
| 6606753 | 11/1966 | Netherlands . |

OTHER PUBLICATIONS

R. Riemschneider et al., Monatsch, 84, p. 518 (1953).

M. S. Newman, et al., Journal of Organic Chemistry, 31, pp. 3980-3983 (1966).

D. G. Crosby, et al., Journal of the American Chemical Society, 76, p. 4458 (1954).

*Primary Examiner*—Henry R. Jiles

*Assistant Examiner*—Robert C. Whittenbaugh

*Attorney, Agent, or Firm*—Robert J. Grassi

[57] ABSTRACT

Novel S-aryl N-halo-alkyl thiolcarbamates, S-aryl N,N-alkyl, halo-alkyl thiolcarbamates, and S-aryl N,N-bis(-halo-alkyl)thiolcarbamates which are useful for controlling the plant pest, Late Blight of Tomatoes, *Phytophthorans infestans*, the intermediates for producing these novel thiolcarbamates, as well as, the method of controlling Late Blight of Tomatoes with the compounds are also disclosed.

14 Claims, No Drawings

N-HALO-ALKYL THIOLCARBAMATES AND N-ALKENYL THIOLCARBAMATES

BACKGROUND OF THE INVENTION

1. Field of the Invention

This invention concerns novel S-aryl N-halo-alkyl thiolcarbamates, S-aryl N,N-alkyl, halo-alkyl thiolcarbamates, and S-aryl N,N-bis-(halo-alkyl)thiolcarbamates, particularly those in which the halo-alkyl has from three to four carbon atoms, and the novel intermediates for producing them.

This invention also concerns a method of controlling the plant pest, *Phytophthorans infestans* with these novel compounds.

2. Description of the Prior Art

Plant pests such as fungi of *Phytophthorans infestans,* continually affect the growth of crops, trees, and other desirable vegetation. One method of controlling plant pests such as fungi is by application of chemicals which affect the fungi. These chemicals are applied to the soil, to the desirable plant, or directly to the fungi itself. Because thousands of species of fungi exist, which differ in tolerance to chemicals, new chemicals must be discovered which are effective to control the deleterious effects of particular fungi.

The prior art as illustrated by the following patents and references shows that different thiolcarbamates may be effective against certain plant pests.

U.S. Pat. Nos. 2,977,209 and 3,265,563 disclose S-phenyl N-alkylthiolcarbamates, S-chlorophenyl N-alkylthiolcarbamates, S-ethoxyphenyl N-allylthiolcarbamate, S-ethoxyphenyl N-alkylthiolcarbamates, S-p-tolyl N-alkylthiolcarbamates, and S-2,4-dimethylphenyl N-alkylthiolcarbamates as herbicides and fungicides. U.S. Pat. No. 3,632,332 discloses S-4-methylbenzyl-N,N-diethylthiocarbamate as a herbicide for rice fields. U.S. Pat. No. 3,301,885 discloses S-substituted phenyl N-alkyl, N-alkoxy thiolcarbamates as herbicides, miticides, and insecticides. U.S. Pat. No. 3,687,653 discloses trifluoromethylbenzyl N-alkylthiolcarbamates as herbicides. U.S. Pat. No. 3,046,189 and Canadian No. 789,575 disclose S-alkyl N-alkylthiocarbamates as nematocides. R. Reimschneider and O. Lorenz, in Monstsch., 84, 518 (1953) describe S-phenyl N,N-dimethylthiolcarbamate, and D. G. Crosby and C. Niemann, *Journal of American Chemical Society,* 76 4458 (1954) describe S-phenyl N-cyclohexylthiolcarbamate, and S-phenyl N-phenylthiolcarbamate. Netherlands Pat. No. 6,606,753 discloses S-phenyl N-trifluoromethylphenylthiocarbamate and S-substituted phenyl N-substituted trifluoromethylphenylthiocarbamates as anthelmintics. M. S. Newman and H. A. Karnes *Journal of Organic Chemistry,* 31, 3980–3983 describe S-β-naphthyl N,N-dimethylthiolcarbamate, S-2-nitrophenyl N,N-dimethylthiolcarbamate, S-3-nitrophenyl N,N-dimethylthiolcarbamate, S-2,4,5-trichlorophenyl N,N-dimethylthiocarbamate, S-3-trifluoromethylphenyl N,N-dimethylthiolcarbamate, S-2,3,5,6-tetramethylpentyl N,N-dimethylthiolcarbamate, S-4-tert-butylphenyl N,N-dimethylthiolcarbamate, S-2-methoxyphenyl N,N-dimethylthiolcarbamate and S-4-methoxyphenyl N,N-dimethylthiolcarbamate. U.S. Pat. No. 3,932,632 discloses insecticides of dithiophosphate compounds mixed with S-aryl N,N-dialkylthiolcarbamates, or S-aryl N,N-dialkylenethiolcarbamates, or S-aryl N,N-dialkynylthiolcarbamates, or S-aryl N,N-(alkyl, alkylene, or alkynyl), (alkyl, alkylene, or alkynyl)thiolcarbamates where the aryl may be a substituted phenyl.

SUMMARY OF THE INVENTION

This invention concerns novel S-aryl N-halo-alkylthiolcarbamates of the general formula:

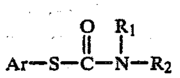

wherein:

- Ar is α-naphthyl, β-napththyl, phenyl, 4-chlorophenyl, 2-chlorophenyl, 3,4-dichlorophenyl, 4-nitrophenyl, 4-fluorophenyl, 4-bromophenyl, 3-methoxyphenyl, 3-methylthiophenyl, 4-methylthiophenyl, 4-alkylphenyl in which the alkyl has from one to four carbon atoms, or 3-alkylphenyl in which the alkyl has from one to four carbon atoms;
- $R_1$ is hydrogen, a straight chain alkyl having from one to three carbon atoms, or a halo-alkyl having from three to four carbon atoms; and
- $R_2$ is a halo-alkyl having from three to four carbon atoms.

These compounds are used to control the plant pest *Phytophthorans infestans,* and this invention relates to this method of controlling this plant pest with these compounds. Examples of these compounds are S-phenyl N-2,3-dibromopropylthiolcarbamate, S-4-nitrophenyl N-2,3-dibromopropylthiolcarbamate, and S-3,4-dichlorophenyl N-2,3-dibromopropylthiolcarbamates. The invention also relates to novel intermediates for producing the above mentioned compositions such as S-4-nitrophenyl N-allylthiolcarbamate.

DESCRIPTION OF THE PREFERRED EMBODIMENTS

The compositions disclosed herein are represented by the general graphic formula (I):

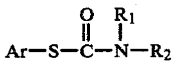

(I)

wherein:

- Ar is an aryl or substituted aryl of α-naphthyl, β-naphthyl, phenyl, 4-chlorophenyl, 2-chlorophenyl, 3,4-dichlorophenyl, 4-nitrophenyl, 4-fluorophenyl, 4-bromophenyl, 3-methoxyphenyl, 3-methylthiophenyl, 4-methylthiophenyl, 4-alkylphenyl in which the alkyl has from one to four carbon atoms, or 3-alkylphenyl in which the alkyl has from one to four carbon atoms,
- $R_1$ is hydrogen, a straight chain alkyl having from one to three carbon atoms, a halo-alkyl having from 3 to 4 carbon atoms, and
- $R_2$ is a halo-alkyl having from three to four carbon atoms.

The phrase "4-alkylphenyl in which the alkyl has from one to four carbon atoms" as used herein and in the claims refers to:

4-methylphenyl, 4-ethylphenyl, 4-n-propylphenyl, 4-isopropylphenyl, 4-n-butylphenyl, 4-sec-butylphenyl, 4-isobutylphenyl, and 4-tert-butylphenyl.

The phrase "3-alkylphenyl in which the alkyl has from one to four carbon atoms" as used herein and in the claims refers to:

3-methylphenyl, 3-ethylphenyl, 3-n-propylphenyl, 3-isopropylphenyl, 3-n-butylphenyl, 3-sec-butylphenyl, 3-isobutylphenyl, and 3-tert-butylphenyl.

The phrase "alkyl having from one to four carbon atoms" as used herein and in the claims refers to:

methyl, ethyl, n-propyl, isopropyl, n-butyl, sec-butyl, isobutyl, and tert-butyl.

The phrase "a straight chain alkyl having from one to three carbon atoms" as used herein and in the claims refers to methyl, ethyl, and n-propyl.

The phrase "halo-alkyl having from three to four carbon atoms" as used herein and in the claims refers to alkyls having from three to four carbon atoms; such as n-propyl, isopropyl, n-butyl, sec-butyl, isobutyl, and tert-butyl, but which have one to all of the hydrogens replaced with a chloro, or bromo atom. Examples of which are:

2-bromopropyl, 2-chloropropyl, 2,3-dibromopropyl, 2,3-dichloropropyl, 2-bromo-2-methylpropyl, 2-chloro-2-methylpropyl, 2-methyl-2,3-dibromopropyl, 2-methyl-2,3-dichloropropyl, 1-methyl-2-bromopropyl, 1-methyl-2-chloropropyl, 1-methyl-2,3-dibromopropyl, 1-methyl-2,3-dichloropropyl, 3-bromobutyl, 3-chlorobutyl, 3,4-dibromobutyl, 3,4-dichlorobutyl, 2,3-dichlorobutyl, and 2,3-dibromobutyl.

Representative examples in which Ar is any of the aryl or substituted aryl mentioned herein, $R_1$ is hydrogen and $R_2$ is a halo-alkyl having from three to four carbon atoms are:

S-α-naphthyl N-2-bromopropylthiolcarbamate;
S-β-naphthyl N-2,3-dibromopropylthiolcarbamate;
S-phenyl N-2,3-dichloropropylthiolcarbamate;
S-4-chlorophenyl N-2-chloropropylthiolcarbamate;
S-2-chlorophenyl N-3-bromobutylthiolcarbamate;
S-3,4-dichlorophenyl N-1-methyl-2,3-dibromopropylthiolcarbamate;
S-4-nitrophenyl N-2,3-dichlorobutylthiolcarbamate;
S-4-fluorophenyl N-2-chloropropylthiolcarbamate;
S-4-bromophenyl N-3,4-dibromobutylthiolcarbamate;
S-3-methylthiophenyl N-2-methyl-2,3-dibromobutylthiolcarbamate;
S-3-methoxyphenyl N-2-methyl-2,3-dichloropropylthiolcarbamate;
S-4-methylthiophenyl N-3,4-dibromobutylthiolcarbamate;
S-4-methylphenyl N-2-methyl-2,3-dichloropropylthiolcarbamate;
S-4-ethylphenyl N-3-bromobutylthiolcarbamate;
S-4-n-propylphenyl N-3-bromobutylthiolcarbamate;
S-4-isopropylphenyl N-2,3-dichlorobutylthiolcarbamate;
S-4-n-butylphenyl N-2,3-dibromobutylthiolcarbamate;
S-4-butylphenyl N-2,3-dichloropropylthiolcarbamate;
S-4-isobutylphenyl N-3,4-dibromobutylthiolcarbamate;
S-4-tert-butylphenyl N-1-methyl-2,3-dichloropropylthiolcarbamate;
S-3-methylphenyl N-2,3-dichlorobutylthiolcarbamate;
S-3-ethylphenyl N-3-chlorobutylthiolcarbamate;
S-3-n-propylphenyl N-3-bromobutylthiolcarbamate;
S-3-isopropylphenyl N-3,4-dichlorobutylthiolcarbamate;
S-3-n-butylphenyl N-3-chlorobutylthiolcarbamate;
S-3-sec-butylphenyl N-1-methyl-2,3-dichloropropylthiolcarbamate; and
S-3-isobutylphenyl N-1-methyl-2-bromopropylthiolcarbamate.

The novel compounds represented by the general formula in which $R_1$ is hydrogen, and $R_2$ is 2,3-dibromopropyl, 2-bromopropyl, 2,3-dibromobutyl, 3,4-dibromobutyl, 3-bromobutyl, and 2,3-dichloropropyl are preferred.

Compounds in which $R_1$ is hydrogen and $R_2$ is 2,3-dibromopropyl are especially preferred; examples of which are:

S-α-naphthyl N-2,3-dibromopropylthiolcarbamate;
S-β-naphthyl N-2,3-dibromopropylthiolcarbamate;
S-phenyl N-2,3-dibromopropylthiolcarbamate;
S-4-chlorophenyl N-2,3-dibromopropylthiolcarbamate;
S-2-chlorophenyl N-2,3-dibromopropylthiolcarbamate;
S-3,4-dichlorophenyl N-2,3-dibromopropylthiolcarbamate;
S-4-nitrophenyl N-2,3-dibromopropylthiolcarbamate;
S-4-methylthiophenyl N-2,3-dibromopropylthiolcarbamate;
S-4-methylphenyl N-2,3-dibromopropylthiolcarbamate;
S-4-ethylphenyl N-2,3-dibromopropylthiolcarbamate;
S-4-n-propylphenyl N-2,3-dibromopropylthiolcarbamate;
S-4-isopropylphenyl N-2,3-dibromopropylthiolcarbamate;
S-4-n-butylphenyl N-2,3-dibromopropylthiolcarbamate;
S-4-isobutylphenyl N-2,3-dibromopropylthiolcarbamate;
S-4-sec-butylphenyl N-2,3-dibromopropylthiolcarbamate;
S-4-tert-butylphenyl N-2,3-dibromopropylthiolcarbamate;
S-3-methylphenyl N-2,3-dibromopropylthiolcarbamate;
S-3-ethylphenyl N-2,3-dibromopropylthiolcarbamate;
S-3-n-propylphenyl N-2,3-dibromopropylthiolcarbamate;
S-3-isopropylphenyl N-2,3-dibromopropylthiolcarbamate;
S-3-n-butylphenyl N-2,3-dibromopropylthiolcarbamate;
S-3-sec-butylphenyl N-2,3-dibromopropylthiolcarbamate;
S-3-isobutylphenyl N-2,3-dibromopropylthiolcarbamate; and
S-3-tert-butylphenyl N-2,3-dibromopropylthiolcarbamate.

Representative examples of thiolcarbamates represented by the general formula in which $R_1$ is one of the alkyl mentioned herein, and $R_2$ is a halo-alkyl mentioned herein are:

S-α-naphthyl N,N-methyl,2-bromopropylthiolcarbamate;
S-β-naphthyl N,N-ethyl,2-chloropropylthiolcarbamate;
S-phenyl N,N-n-propyl,2,3-dibromopropylthiolcarbamate;
S-4-chlorophenyl N,N-methyl,2,3-dibromobutylthiolcarbamate;
S-2-chlorophenyl N,N-n-propyl,2-methyl-2,3-dibromopropylthiolcarbamate;
S-3,4-dichlorophenyl N,N-ethyl,2,3-dichloropropylthiolcarbamate;
S-4-nitrophenyl N,N-n-propyl,1-methyl-2,3-dichloropropylthiolcarbamate;
S-4-fluorophenyl N,N-methyl,2-methyl-2,3-dichloropropylthiolcarbamate;
S-4-bromophenyl N,N-ethyl,2-bromopropylthiolcarbamate;
S-3-methylthiophenyl N,N-n-propyl,2-chloropropylthiolcarbamate;

S-3-methoxyphenyl N,N-methyl,2,3-dibromobutylthiolcarbamate;
S-4-methylthiophenyl N,N-ethyl,2,3-dibromobutylthiolcarbamate;
S-4-methylphenyl N,N-n-propyl,2,3-dichloropropylthiolcarbamate;
S-4-ethylphenyl N,N-methyl-1-methyl-2-chloropropylthiolcarbamate;
S-4-n-propylphenyl N,N-ethyl,1-methyl-2,3-dibromopropylthiolcarbamate;
S-4-isopropylphenyl N,N-n-propyl,1-methyl-2,3-dichloropropylthiolcarbamate;
S-4-n-butylphenyl N,N-methyl,2-methyl-2,3-dibromopropylthiolcarbamate;
S-4-sec-butylphenyl N,N-ethyl,2,3-dichlorobutylthiolcarbamate;
S-4-isobutylphenyl N,N-n-propyl,3,4-dibromobutylthiolcarbamate;
S-4-tert-butylphenyl N,N-n-propyl,3,4-dichlorobutylthiolcarbamate;
S-3-methylphenyl N,N-methyl-2,3-dichloropropylthiolcarbamate;
S-3-ethylphenyl N,N-ethyl,2,3-dibromobutylthiolcarbamate;
S-3-n-propylphenyl N,N-n-propyl,2-chloropropylthiolcarbamate;
S-3-isopropylphenyl N,N-methyl,2-bromopropylthiolcarbamate;
S-3-n-butylphenyl N,N-ethyl,2-chloropropylthiolcarbamate;
S-3-sec-butylphenyl N,N-n-propyl,2,3-dibromopropylthiolcarbamate;
S-3-isobutylphenyl N,N-methyl,2,3-dichloropropylthiolcarbamate; and
S-3-tert-butylphenyl N,N-3-bromobutylthiolcarbamate.

Those compounds in which $R_1$ is a straight chained alkyl of from one to three carbon atoms of methyl, ethyl, or n-propyl, and $R_2$ is 2,3-dibromopropyl are preferred, and those in which $R_1$ is methyl and $R_2$ is 2,3-dibromopropyl are especially preferred.

Of the compounds in which Ar is any of aryls or substituted aryls mentioned herein, $R_1$ is a halo-alkyl mentioned herein, and $R_2$ is a halo-alkyl mentioned herein, those compounds are preferred in which $R_1$ and $R_2$ are the same, or different and have three to four carbon atoms, which are selected from the halo-alkyl group of 2-chloropropyl, 2-bromopropyl, 2,3-dichloropropyl, 2,3-dibromopropyl, 2-chloro-2-methylpropyl, 2-bromo-2-methylpropyl, 2-methyl-2,3-dichloropropyl, and 2-methyl-2,3-dibromopropyl.

Those compounds are especially preferred wherein both $R_1$ and $R_2$ are the same. Representative compounds of which are:

S-α-naphthyl N,N-bis(2-chloropropyl)thiolcarbamate;
S-phenyl N,N-bis(2-bromopropyl)thiolcarbamate;
S-4-chlorophenyl N,N-bis(2,3-dibromopropyl)thiolcarbamate;
S-2-chlorophenyl N,N-bis(2,3-dichloropropyl)thiolcarbamate;
S-3,4-dichlorophenyl N,N-bis(2-chloro-2-methylpropyl)thiolcarbamate;
S-4-nitrophenyl N,N-bis(2-bromo-2-methylpropyl)thiolcarbamate;
S-4-fluorophenyl N,N-bis(2-methyl-2,3-dichloropropyl)thiolcarbamate;
S-4-bromophenyl N,N-bis(2-methyl-2,3-dibromopropyl)thiolcarbamate;
S-3-methylthiophenyl N,N-bis(2-methyl-2,3-dibromopropyl)thiolcarbamate;
S-3-methoxyphenyl N,N-bis(2,3-dibromopropyl)thiolcarbamate;
S-4-methylthiophenyl N,N-bis(2-methyl-2,3-dichloropropyl)thiolcarbamate;
S-4-methylphenyl N,N-bis(2-methyl-2,3-dibromopropyl)thiolcarbamate;
S-4-n-butylphenyl N,N-bis(2-bromo-2-methylpropyl)thiolcarbamate;
S-4-tert-butylphenyl N,N-bis(2-chloro-2-methylpropyl)thiolcarbamate;
S-4-sec-butylphenyl N,N-bis(2,3-dibromopropyl)thiolcarbamate;
S-4-isobutylphenyl N,N-bis(2,3-dichloropropyl)thiolcarbamate;
S-4-n-propylphenyl N,N-bis(2-bromopropyl)thiolcarbamate;
S-4-isopropylphenyl N,N-bis(2-chloropropyl)thiolcarbamate;
S-4-ethylphenyl N,N-bis(2-bromopropyl)thiolcarbamate; and
S-3-tert-butylphenyl N,N-bis(2,3-dichloropropyl)thiolcarbamate.

Those compounds wherein Ar is any of the aryls or substituted aryls mentioned herein, $R_1$ and $R_2$ are the same and are 2,3-dibromopropyl, 2,3-dichloropropyl, 2-methyl-2,3-dibromopropyl, or 2-methyl-2,3-dichloropropyl, are highly preferred. Some specific compounds representative of these highly preferred compounds are:

S-β-naphthyl N,N-bis(2,3-dichloropropyl)thiolcarbamate;
S-α-naphthyl N,N-bis(2,3-dibromopropyl)thiolcarbamate;
S-phenyl N,N-bis(2,3-dibromopropyl)thiolcarbamate;
S-3-methylphenyl N,N-bis(2,3-dichloropropyl)thiolcarbamate;
S-3-n-propylphenyl N,N-bis(2-methyl-2,3-dibromopropyl)thiolcarbamate;
S-3-tert-butylphenyl N,N-bis(2-methyl-2,3-dichloropropyl)thiolcarbamate; and
S-3-sec-butylphenyl N,N-bis(2,3-dichloropropyl)thiolcarbamate.

Especially preferred as those compounds in which Ar is any of the aryls or substituted aryls mentioned herein, and both $R_1$ and $R_2$ are 2,3-dibromopropyl.

SYNTHESIS OF THE COMPOUNDS

Those S-aryl N-halo-alkylthiolcarbamates of the general formula:

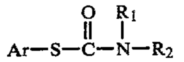

wherein:

$R_1$ is hydrogen and $R_2$ is a halo-alkyl are easily made by bromination, or chlorination of S-aryl N-alkenylthiolcarbamates of the general formula:

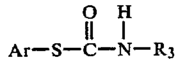

wherein:

Ar is the same as mentioned hereinbefore and $R_3$ is an alkenyl of from three to four carbon atoms.

Most of these S-aryl N-alkenylthiolcarbamates are novel compositions useful as intermediates, to form the S-aryl N-halo-alkylthiolcarbamates. These S-aryl N-alkenylthiolcarbamates are made by the reaction of an alkenylisocyanate of the general formula O═C═N—$R_3$ and an arylthiol of the general formula Ar—S—H, wherein Ar and $R_3$ are as defined hereinbefore.

The phrase "an alkenyl of from three to four carbon atoms" as used herein and in the claims refers to alkenyls such as:

allyl, 2-butenyl, 3-butenyl, 2-methyl-2-propenyl, and 1-methyl-2-propenyl.

Preferably $R_3$ is a straight chain alkenyl of from three to four carbon atoms, and especially preferred are the alkenyls of allyl, and 2-methyl-2-propenyl, with allyl being the most preferred alkenyl.

The following specific Examples I to VI illustrate the synthesis of certain of these compounds by the reaction of the arylthiols having aryls mentioned herein with isocyanates having halo-alkyl, or alkenyls mentioned herein.

EXAMPLE I

Synthesis of S-3,4-dichlorophenyl-N-allylthiolcarbamate

A solution of 3,4-dichlorobenzenethiol (8.6 grams, 48 millimoles), triethylamine (1–2 drops) in 50 milliliters of anhydrous ethylether was placed into a 250 milliliter, three-necked flask. This flask was equipped with a power driven Trubore glass stirrer having a Teflon blade, an addition funnel, a Claisen type adapter fitted with a reflux condenser and thermometer. A heating mantle was placed around the flask. Allylisocyanate (4.0 grams, 48 millimoles) was placed in the addition funnel, and added dropwise to the stirred ethylether solution over a 10 minute period. After the addition, the reaction mixture was refluxed for 2 hours; the solvent (ethylether) was evaporated, to give a 9.0 grams (71.5 percent yield) of a white crystalline material having a melting point of 107°–108.5° Centigrade (S-3,4-dichlorophenyl N-allylthiolcarbamate). This had an infrared spectrum with a N-H band at 3300 centimeters$^{-1}$, and a C═O band at 1650 centimeters$^{-1}$.

EXAMPLE II

S-phenyl N-allylthiolcarbamate

The procedure of Example I was followed using 11.0 grams of benzenethiol (0.1 mole) and 8.3 grams of allylisocyanate (0.1 mole) to obtain a pale yellow liquid (19.4 grams, 100 percent yield) which had an infrared spectra with a N-H band at 3300 centimeters$^{-1}$, and a C═O band at 1660 centimeters$^{-1}$.

EXAMPLE III

S-4-nitrophenyl N-allylthiolcarbamate

The procedure of Example I was followed using 3.0 grams of allylisocyanate (36 millimeters) and 6.0 grams of 4-nitrobenzenethiol which was purified by an azeotropic distillation with 125 milliliters of benzene. A yellow crystalline material (6.9 grams, 88.5 percent yield) formed when the reaction mixture stood overnight in a hood. The yellow crystalline material was not recrystallized from benzene as in Example I. The yellow crystalline material had a melting point of 122°–124° Centigrade, and an infrared spectrum with a N-H band at 3310 centimeters$^{-1}$, and a C═O band at 1650 centimeters$^{-1}$.

The novel S-aryl N-allylthiolcarbamate, S-aryl N,N-diallylthiolcarbamates, and other S-aryl N-alkenylthiolcarbamates and S-aryl N,N-di(alkenyl)thiolcarbamates disclosed herein, are intermediates for the preparation of S-aryl N-halo-substituted alkylthiolcarbamates and S-aryl N,N-di(halo-substituted alkyl)thiolcarbamates mentioned herein.

EXAMPLE IV

S-phenyl N-2,3-dibromopropylthiolcarbamate

S-phenyl N-allylthiolcarbamate (9.7 grams, 0.05 mole) from Example II was dissolved in carbon tetrachloride (150 milliliters) and the solution was cooled to 0° Centigrade. A solution of bromine (8.0 grams, 0.05 gram atom) in 75 milliliters of carbon tetrachloride was slowly added (1.5 hours) at 0°–5° Centigrade to the cooled solution of S-phenyl N-allylthiolcarbamate. The reaction mixture was warmed to room temperature, washed with 100 milliliters of 10 weight percent aqueous solution of sodium bisulfite, then with 100 milliliters of water, and dried with sodium sulfate ($Na_2SO_4$). The solvent was removed to give 12.1 grams (69 percent yield) of a clear, colorless, viscous liquid which did not crystallize. This liquid had an infrared spectrum with a N-H band at 3300 centimeters$^{-1}$ and a C═O band at 1650 centimeters$^{-1}$. The NMR spectrum showed the loss of the double bond.

EXAMPLE V

S-3,4-dichlorophenyl N-2,3-dibromopropylthiolcarbamate

The procedure of Example IV was followed using chloroform as the solvent, and 6.5 grams (25 millimoles) of S-3,4-dichlorophenyl N-allylthiolcarbamate from Example I and 4.0 grams (0.025 gram atoms) of bromine. This gave 9.6 grams (91.5 percent yield) of a colorless viscous oil, which crystallized upon standing. Recrystallization from 100 milliliters benzene gave 5.6 grams of a white crystalline material having a melting point of 114°–118° Centigrade, and an infrared spectrum with a N-H band at 3300 centimeters$^{-1}$ and a C═O band at 1655 centimeters$^{-1}$.

EXAMPLE VI

S-4-nitrophenyl N-2,3-dibromopropylthiolcarbamate

The procedure of Example IV was followed using chloroform as a solvent, 4.8 grams (20 millimoles) of S-4-nitrophenyl N-allylthiolcarbamate (from Example V) and 3.2 grams (0.02 gram atoms) of bromine to form 6.8 grams (85 percent yield) of a yellow crystalline material. Recrystallization of this material from 100 milliliters benzene gave 5.3 grams of a pale yellow crystalline material with a melting point of 112°–119° Centigrade, and an infrared spectrum with a N-H band at 3490 centimeters$^{-1}$ and a C═O band at 1650 centimeters$^{-1}$.

In the synthesis of the intermediate S-aryl N-alkenylthiolcarbamates with up to four carbon atoms, other inert solvents which dissolve the reactants and products, and which are easily removed from the products by evaporation, drying, filtering, or washing, and which have a boiling point appropriate to the reaction temperatures may be used in lieu of ethylether. Examples are tetrahydrofuran, hexane, and benzene. The reaction temperature may vary from 0° Centigrade to the boiling point of the refluxing mixture. Preferably the reaction temperature range is from 0° C. to 80° C.

The bromination reaction solvent is one which is readily removed from the product, dissolves the bromine, reactant or product and has a boiling point appropriate to the bromination reaction temperature. Examples of such solvents are carbon tetrachloride, Freons, $CCl_3Br$ and $CCl_2Br_2$, chloroform, and methylene chloride. The bromination reaction temperature may vary from −10° C. to +50° C.

As an alternative synthesis, an isocyanate of a lower halo-substituted alkyl such as 2,3-dibromopropylisocyanate could be used in lieu of allylisocyanate to form S-aryl N-halo substituted alkylthiolcarbamates such as S-3-methoxyphenyl N-2,3-dibromopropylthiolcarbamate. The allylisocyanate may be brominated to 2,3-dibromopropylisocyanate prior to reacting with the S-3-methoxybenzenethiol.

Removal of the solvents, and reactants or other impurities from the arylthiolcarbamates such as S-3-methoxyphenyl N-2,3-dibromopropylthiolcarbamate is not necessary except insofar as they interfere with the intended use of the compound; such as systemic control of nematodes. All conventional purification techniques such as recrystallization from solvents, fraction crystallization, washing with one or more solvents, followed by evaporation of the solvents, filtration from the solvents, or their equivalents may be used.

Other routes may be used for synthesis of the S-arylthiolcarbamates disclosed herein. For example, S-4-nitrophenylthiolchloroformate may be reacted with allylamine in an inert solvent mentioned herein in the presence of a stoichiometric amount of an acid acceptor at temperatures from 15° to 100° C., to form the S-4-nitrophenyl N-allylthiolcarbamate which is then brominated. Alternatively, 2,3-dibromopropylamine may be substituted for allylamine.

Another synthesis route is by the reaction of an arylthiolchloroformate of the general formula:

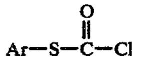

with an amine of the general formula:

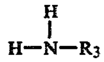

to produce alkenylthiolcarbamates of the general formula:

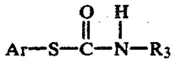

wherein Ar and $R_3$ are as defined hereinbefore.

The synthesis of the thiolcarbamates of the general formula:

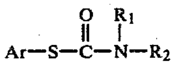

may also be accomplished by the reaction of an arylthiolchloroformate of the general formula:

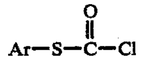

mentioned hereinbefore, and an amine of the general formula:

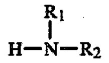

wherein Ar, $R_1$, and $R_2$ are as defined hereinbefore.

Those arylthiolcarbamates of the general formula:

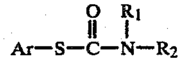

in which $R_1$ and $R_2$ are both halo-alkyls, may be made by bromination or chlorination of S-aryl N-alkenylthiolcarbamates of the general formula:

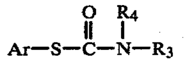

wherein $R_3$ is as defined hereinbefore and $R_4$ is an alkenyl of from three to four carbon atoms.

These N-alkenylthiolcarbamates of the general formula:

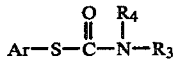

are themselves novel compositions and useful intermediates.

The compounds in which $R_3$ and $R_4$ are straight chained alkenyls of from three to four carbon atoms are preferred; especially those in which $R_3$ and $R_4$ are allyl and 2-methyl-2-propenyl with allyl being preferred. Those compounds in which $R_3$ and $R_4$ are the same are especially preferred.

SYNTHESIS OF THE INTERMEDIATES

The following procedure illustrates the synthesis of these S-aryl N-alkenyl and S-aryl N-halo-alkylthiolcarbamates by the reaction of arylthiolchloroformates having an aryl mentioned herein and an alkyleneamine, dialkyleneamine, halo-alkylamine or bis(halo-alkyl)amine, having an alkylene, or halo-alkyl mentioned herein.

SYNTHESIS OF S-ARYL N,N-DIALLYLTHIOLCARBAMATE

A 250 milliliter, three-necked flask is equipped with a power driven Trubore glass stirrer having a Teflon blade, an addition funnel and a Claisen type adapter fitted with a reflux condenser and thermometer. A heating mantle is placed around the flask. A solution of 1.50 grams (0.0154 moles) of diallylamine, and 1.30 grams (0.0128 mole) of triethylamine in 50 milliliters of benzene is placed in the flask. A solution of 0.0128 mole of S-arylthiolchloroformate of the general formula:

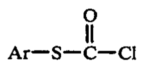

in 25 milliliters of benzene is placed in the addition funnel. This solution of arylthiolchloroformate is slowly added (dropwise over a 15 minute period) to the vigorously stirred diallylamine solution. During the addition, the temperature will rise above ambient. After the addition, the reaction mixture is refluxed at 80° Centigrade for one hour, cooled to ambient temperature and filtered to remove the white crystalline triethylamine hydrochloride salt. This filtrate of the benzene reaction mixture is washed with 100 milliliters of 2 weight percent aqueous hydrochloric acid solution, and then with 150 milliliters of water. It is then dried with anhydrous magnesium sulfate ($MgSO_4$) and refiltered. The solvent is removed from the filtrate under reduced pressure on a rotary evaporator to give the S-aryl N,N-diallylthiolcarbamate.

SYNTHESIS OF S-ARYL N,N-BIS(2,3-DIBROMOPROPYL)THIOLCARBAMATE

Liquid bromine (4.1 grams, 0.0256 moles) is slowly added dropwise over a 20 minute period to a vigorously stirred, cooled (−5° to 0° Centigrade) solution containing the S-aryl N,N-diallylthiolcarbamate (synthesis as above, 0.0128 moles) in 75 milliliters of carbon tetrachloride or other solvent in which the compound is soluble. The reaction mixture is stirred and maintained at −5° to 0° Centigrade for two hours and then at ambient temperature for one hour. Afterwards the reaction solvent is removed by evaporating the mixture under reduced pressure on a rotary evaporator.

In the synthesis of the intermediate S-aryl N,N-diallylthiolcarbamate, other inert solvents which dissolve the reactants and products, and which are easily removed from the products by evaporation, drying, filtering, or washing, and which have a boiling point appropriate to the reaction temperatures may be used in lieu of benzene. Examples are tetrahydrofuran, ethylether, hexane, and chloroform. The reaction temperature may vary from 0° C. to the boiling point of the refluxing mixture. Preferably the reaction temperature range is from 0° C. to 80° C.

The bromination reaction solvent is one which is readily removed from the product, dissolves the bromine, reactant or product, and has a boiling point appropriate to the bromination reaction temperature. Examples of such solvents are: carbon tetrachloride, chloroform, methylene chloride, $CCl_3Br$, and $CCl_2Br_2$. The bromination reaction temperature may vary from −10° C. to +50° C.

As an alternative synthesis of S-aryl N,N-bis(2,3-dibromopropyl)thiolcarbamate, diallylamine may first be brominated to form bis(2,3-dibromopropyl)amine which could then be reacted with S-arylthiolchloroformate.

Removal of the solvents, and reactants or other impurities from the S-aryl N,N-bis(2,3-dibromopropyl)thiolcarbamate of S-aryl N,N-diallylthiolcarbamate is not necessary except in so far as they interfere with the intended use of the compounds; such as the use of S-3-methoxyphenyl N,N-bis(2,3-dibromopropyl)thiolcarbamate for control of Late Blight of Tomatoes. All conventional purification techniques, such as recrystallization from solvents, fractional crystallization, washing with one or more solvents, followed by evaporation of the solvents, or filtration from the solvents, or their equivalents may be used.

SYNTHESIS OF THE OTHER COMPOUNDS DISCLOSED HEREIN

The other compounds disclosed herein may also be synthesized by the reaction of the aryl thiochloroformates formed from phosgene and the appropriate arylthiols (U.S. Pat. No. 3,165,544) with amines having the appropriate alkylene or halo-substituted alkyl, mentioned herein.

The reaction temperature for the reaction of the thiochloroformates and amines may vary from 0° to 50° Centigrade.

In lieu of triethylamine other tertiary amines may be used in the reaction of the thiochloroformates and amines, such as trimethylamine, tripropylamines or trialkylamines in which the alkyl has up to 5 carbon atoms, or other proton acceptors may be used such as pyridine, alkyl substituted pyridines, sodium hydroxide, and potassium hydroxide.

Alternatively, the halo-alkylamines, alkenylamines, or dialkenylamines having an alkenyl mentioned herein could be reacted with phosgene to form the corresponding alkenylcarbamoyls, halo-alkyl carbamoyls, or dialkenylcarbamoyls. These carbamoyls are then reacted with the appropriate arylthiol mentioned herein. These reactions may be carried out in the inert solvents mentioned herein, containing a stoichiometric amount of the acid acceptor mentioned herein, at the temperature ranges mentioned herein, to form the thiolcarbamates mentioned herein.

The following procedure illustrates the synthesis route in which thioaryls having an aryl mentioned herein are reacted with carbamoyl chloride having one or two halo-alkyl or alkenyl mentioned herein.

SYNTHESIS OF S-3-METHYLPHENYL N,N-DIALLYLTHIOLCARBAMATE

A 5 milliliter anhydrous ethylether solution of an alkenyl-carbamoyl chloride, e.g., diallylcarbamoyl chloride (50 millimoles) and a 5 milliliter anhydrous ethylether solution of triethylamine (50 millimoles) are simultaneously added over a 40 minute period at ambient temperature to a stirred forty (40) milliliter anhydrous ethylether solution of 3-thiocresol (50 millimoles). The reaction mixture is stirred and refluxed for two and one-half (2½) hours and cooled to room temperature and then poured in 100 milliliters of distilled water. The organic layer and aqueous layer are separated, and the aqueous layer is extracted with ethylether, which extracts are combined with the organic layer. The combined ether extracts and organic layer are washed with 100 milliliters of a 10 weight percent aqueous solution of sodium hydroxide (NaOH), then with 100 milliliters of a 10 weight percent aqueous hydrochloric acid solution, and then dried with sodium sulfate ($Na_2SO_4$) and filtered, and the solvent is removed on a rotary evaporator to give the crude product which can be further refined by crystallization.

PROPERTIES

The following test results illustrate the control of the disease Late Blight of Tomatoes by the novel S-arylthiolcarbamates of the general formula:

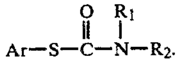

TEST PROCEDURE

The disease is caused by the fungus *Phytophthora infestans.* The test procedure determines protectant properties of a compound; that is, whether the compound prevents plants from the effects of the disease, if the plants are contacted with the compound prior to exposure to the causal fungus.

In the test, Bonny Best tomato plants, approximately five to six weeks old in five leaf growth stage grown under natural sunlight in a glass covered greenhouse were mounted on a compound turntable and sprayed to incipient run off at 40 pounds pressure for 60 seconds at a rate equivalent to 50 gallons per acre, using a solid cone, T-Jet 8001-E spray nozzle tip.

For the tests a pre-determined amount of test compound was dissolved in a stock solution, the volume of which was equivalent to 19 percent by volume of the total spray volume using 90 percent by volume distilled water. The stock solution was an acetone emulsion solution, containing 1995 ml. acetone, 4 ml SPAN 85 ® (sorbitan trioleate), and 1 ml. TWEEN 80 ® (sorbitan monooleate polyalkylene derivative).

After the treated plants had dried, (4–8 hours), they were inoculated by uniformly spraying at a rate of 100 milliliters of a suspension containing $10^5$ sporangia and $10^6$ zoaspores of the fungus *Phytophthora infestans,* taken directly from diseased plants per 35 tomato plants. Then the plants were incubated in the dark at 70° F. and 95 percent or more relative humidity for about 40 hours, which normally insures that the spores have a chance to infest the plants and then the plants were placed in a glass greenhouse, which used natural sunlight, and were observed for signs of developed infection lesions (which were visible to the naked eye) of the top three leaves. These generally occured after 3 to 5 days. The greenhouse operates at a temperature from 70° to 80° F. and a humidity range of from 50 to 90 percent.

The severity of the disease was determined by actual count of the developed lesions on inoculated but otherwise untreated controls. The test results are expressed as Control Effectiveness, which is determined by actual amount of the number of developed lesions appearing on the respectively treated plants compared directly to equivalent developed lesions on inoculated but otherwise untreated controls. This control effectiveness is expressed as Percent Control which is calculated as follows:

$$\%\ \text{control} = 100\% - 100\% \frac{(\text{number of lesions for all treated plants})}{(\text{number of lesions for all control plants})}$$

The foliar fungicidal test results are given in Table 1. Column 1 of Table 1 gives the Example number; column 2 lists the test compound, which is prepared according to the synthesis given herein unless indicated otherwise; column 3 gives the percent control obtained at 1,000 parts per million (ppm).

For some compounds, the values of repeated tests were given, as well as, values at lower test concentrations.

TABLE 1

| Example No. | Compound Applied | Percent Control of Late Blight of Tomatoes |
|---|---|---|
| VII | S-β-naphthyl N,N-dimethylthiolcarbamate[d] | 51 |
| VIII | S-phenyl N-methylthiolcarbamate[h] | 0 |
| IX | S-phenyl N-ethylthiolcarbamate[h] | 0[a]<br>0[b]<br>0[c] |
| X | S-phenyl N-2,3-dibromopropylthiolcarbamate | 61 |
| XI | S-4-chlorophenyl N-methylthiolcarbamate[h] | 0[i] |
| XII | S-4-chlorophenyl N,N-diallylthiolcarbamate[e] | 0 |
| XIII | S-4-nitrophenyl N-2,3-dibromopropylthiolcarbamate | 76 |
| XIV | S-4-methoxyphenyl N-allylthiolcarbamate | 0 |
| XV | S-4-methoxyphenyl N,N-dimethylthiolcarbamate | 0 |
| XVI | S-3,4-dichlorophenyl N-2,3-dibromopropylthiolcarbamate | 76 |

[a]test results at test concentration of 500 ppm
[b]test results at test concentration of 250 ppm
[c]test results at test concentration of 250 ppm
[d]known compound—Journal of Organic Chemistry, 31, pages 3980–3983
[e]known compound described in U.S. Pat. No. 2,977,209
[h]known compound described in U.S. Pat. Nos. 2,977,209 and 3,265,563, and claimed for use as a systemic nematocide in Applicant's copending application entitled Systemic Nematocide, Serial No. 408,775, filed October 23, 1973.
[i]"Zero" (0) percent control at 500 ppm and below for all diseases or remaining diseases described in this table.

APPLICATION a. Suitable Agricultural Formulations

The compounds disclosed herein may themselves be applied directly to the area where the deleterious effects of the plant pests are to be controlled. It is, however, preferable to use suitable agricultural formulations which contain other ingredients which enhance application of the compound. These agricultural formulations will generally comprise from 5 percent to 95 percent or more by weight of S-arylthiolcarbamate, of the general formula:

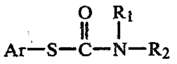

disclosed herein, or mixtures of these compounds, and either from 1 percent to 95 percent by weight of an agricultural diluent, or from 1 percent to 20 percent by weight of a surface active agent and other ingredients required to produce wettable powders, dusts, solutions, emulsifiable concentrates, granules, and the like, or both.

Wettable powders will contain from 25 to 80 percent active ingredients, from 0.1 percent to 5.0 percent wetters and dispersants with the balance consisting of inorganic absorptive diluents.

Since some compounds are solids, other are liquids, and others are viscous materials, they may be dissolved in one or more solvents and then sprayed upon the absorptive diluents of attapulgite clay, synthetic fine silica, and synthetic calcium and sodium alumino-silicates, or other solid insecticides, or foliar fungicides mentioned herein and then the solvent or solvents are evaporated off.

Emulsifiable oils will contain from 20 percent to 97 percent active ingredient, from 3.0 to 10.0 percent of an emulsifying agent, and may also contain from 1 percent to 77 percent water-immiscible solvent such as xylene or alkylated naphthalene.

Granules will contain from 5 percent to 25 percent active ingredient, and may also contain from 1 percent to 20 percent of a surfactant extended upon a granular base such as vermiculite or granular attapulgite. Granules produced by extrusion or tumbling will contain like amounts of active ingredient and surfactant.

b. Combinations With Other Insecticides and Fungicides

For the control of a wider range of crop-pests and diseases it is sometimes desirable to combine one or more of the thiolcarbamates of the general formula:

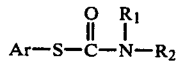

with from 0.05 to 4 parts by weight of insecticides and fungicides, etc., known to be effective against crop-pests and diseases in concentrated premix or during the application step for foliar applications. Examples of other pesticides are: granules containing stable metal azide-metal salt formulations disclosed in assignee's copending application entitled AZIDE-METAL SALT FORMULATIONS, Ser. No. 624,357, filed Oct. 21, 1975, containing S-4-methoxyphenyl N-2,3-dibromopropylthiolcarbamate, disclosed is assignee's copending application entitled S-p-METHOXYPHENYL N-BIS-2,3-DIBROMOPROPYLTHIOLCARBAMATE, Ser. No. 631,751, filed Nov. 7, 1975, or S-4-methoxyphenyl N,N-bis(2,3-dibromopropyl)thiolcarbamate disclosed in assignee's copending application entitled S-p-METHOXYPHENYL N,N-DIALLYLTHIOLCARBAMATE and S-p-METHOXYPHENYL N,N-BIS(2,3-DIBROMOPROPYL)THIOLCARBAMATE, Ser. No. 631,802, filed Nov. 7, 1975, Sevin 1(naphthyl-N-methylcarbamate), Chlorobenzilate (ethyl 4,4'-dichlorobenzilate), Guthion (O,O-diethyl-S-[4-oxo-1,2,3-benzotriazin-3(4H)-ylmethyl]phosphorodithioate), Disyston (O,O-diethyl-S-[2-(ethylsulfinyl)ethyl]phosphorodithioate), Maneb (manganous ethylene bisdithiocarbamate), Karathane (mixture of 2,4-dinitro-6-octylphenylcrotonate, 2,6-dinitro-4-octylphenylcrotonate, nitrooctylphenols (principally dinitro), 4-(1-methylheptyl)2,6-dinitrophenylcrotonate, 4-(1-ethylhexyl)2,6-dinitrophenylcrotonate, 4-(1-propylpentyl)2,6-dinitrophenylcrotonate, 6-(1-methylheptyl)-2,4-dinitrophenylcrotonate, 6-(1-ethylhexyl)2,4-dinitrophenylcrotonate, and 6-(1-propylpentyl)2,4-dinitrophenylcrotonate), Blasticidin (blasticidin-S-benzylaminobenzenesulfonate), Benlate (methyl 1-(butylcarbamoyl)-2-benzimidazolecarbamate), or Plantvax (5,6-dihydro-2-methyl-1,4-oxathiin-3-carboxanilide-4,4-dioxide).

In some instances it is also desirable to include special purpose additives which will inhibit corrosion, reduce foaming, reduce caking, or increase flocculation.

The following example illustrates a suitable emulsifiable concentrate formulation, for dilution in water for spraying plants, particularly, plant foliage or for application to other plant parts as herein mentioned. In this emulsifiable concentrate formulation, the percentages are weight percent.

EXAMPLE XVII

Emulsifiable Concentrate Formulations

| | |
|---|---|
| 3,4-dichlorophenyl N-(2,3-dibromopropyl)thiolcarbamate | 13% |
| Xylene | 41% |
| Isophorone | 41% |
| ATLOX® 3404* | 1% |
| ATLOX® 3403 F* | 4% |

*Commercial emulsifier for agricultural pesticides manufactured by Atlas Powder Co., Wilmington, Delaware, and registered with the U.S. Food and Drug Administration.

C. Amount of the Compounds Described Herein to Apply

The novel compounds described herein when used for a fungicide, to control Late Blight of Tomatoes (*Phytophthorans infestans*), are applied in an amount effective to control the plant pest. The phrase "an amount effective to control the plant pest" as used herein and in the claims means that amount which will vary with the season of the year, the weather, and the severity of the disease, needed to reduce the percentage of plants having the disease from 10 to 100 percent. The fungus plant pests controlled include those specifically described and shown herein as well as equivalent species which are biologically related such as those of the genus *Phytophthorans* which may be controlled by application of the compounds.

A single compound may be used in the formulation described herein, preferably a plurality of the compounds are used together either in a formulation or by concurrent application, that is applying one or more of the compounds to the plant itself. In other applications, one or more compounds may be applied to the plant, and within about 10 days, the one or more of same compounds, or different compounds may be applied to the plant so as to effectively control plant pests.

When the compounds of the general formula

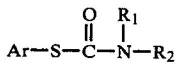

are applied as a foliar fungicide, the amount effective to control the plant pest are those application rates of from 20 parts per million to the amount tolerated by plant, generally from 500 to 10,000 parts per million (ppm) of one or more of the active compounds, applied as a solution to the point of run off, or as a powder or dust which thinly coats the plant part desired to be covered.

Those compounds in which $R_1$ is hydrogen, and $R_2$ is 2-bromopropyl, 2,3-dibromopropyl, 2,3-dichloropropyl, 3,4-dibromobutyl, or 3-bromobutyl are preferred for application at lower rates such as 50 to 7,500 parts per million (ppm). Those in which $R_2$ is 2,3-dibromopropyl may be used at concentrations from 500 to 4,000 parts per million (ppm). Those in which $R_1$ is a straight chain alkyl of from one to three carbons may be used at concentrations from 20 to 9000 parts per million (ppm). Those in which $R_1$ and $R_2$ are both straight chained halo-alkyls of from three to four carbon atoms may be used at concentrations from 20 to 5000 parts per million (ppm). Those compounds in which $R_1$ and $R_2$ are both 2,3-dibromopropyl may be used at concentrations between 20 and 4000 parts per million (ppm).

d. Application To Control Other Plant Pests

Although the novel compounds of the general formula

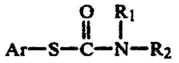

are used to control Late Blight of Tomatoes, this does not preclude their use against other plant pests such as for systemic control of the deleterious effects of Meloidogyne nemas species such as *Meloidogyne incognita, Meloidogyne exigua* (Coffee Root-knot Nematode), *Meloidogyne arenaria* (Peanut Root-knot Nematode), *Meloidogyne hapla* (Northern Root-knot Nematode), and Citrus root Nematode.

Other species of nematodes may be controlled by applications other than systemic foliage contact, for example, by supplying the compounds having activity against the harmful effects of nematodes to the soil, by dipping the bulbs in solutions. Some examples of these other nematodes are:

| | |
|---|---|
| Aphelenchoides species | Bud and Leaf Nematodes |
| *Anguina tritici* | Wheat Nematode |
| *Anguina agrostis* | Grass Nematode |
| Belonolaimus species | Sting Nematodes |
| Criconemoides species | Ring Nematodes |
| *Ditylonchus dipsaci* | Stem and Bulb Nematode |
| *Ditylonchus destructor* | Potato Rot Nematode |
| *Ditylonchus angustus* | Rice Nematode |
| *Dolichodorus heterocephalus* | Awl Nematode |
| Helicotylenchus species | Spiral Nematodes |
| *Heterodera rostochiensis* | Golden Nematode |
| *Heterodera tabacum* | Tobacco Cyst Nematode |
| *Heterodera schachtii* | Sugar Beet Nematode |
| *Heterodera carotae* | Carrot Root Nematode |
| *Heterodera gottingiana* | Pea Root Nematode |
| *Heterodera glycines* | Soybean Cyst Nematode |
| Hopolaimus species | Lance Nematodes |
| *Pratylenchus brachyurus* | Smooth-headed Lesion Nematode |
| Pratylenchus species | Meadow Nematodes |
| *Pratylenchus musicola* | Banana Nematode |
| *Pratylenchus zeae* | Corn Nematode |
| *Radopholus similis* | Burrowing Nematode |
| *Rotylenchus reniformis* | Kidney-shaped Nematode |
| Trichodorus species | Stubby-root Nematode |
| *Tylenchorhynchus claytoni* | Tobacco Stunt Nematode |
| Xiphinema species | Dagger Nematodes |

While the invention has been described with reference to specific details of certain illustrative embodiments, it is not intended that it shall be limited thereby except insofar as such details appear in the accompanying claims.

I claim:

1. A compound represented by the general formula

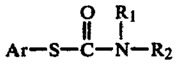

wherein:

Ar is selected from the group consisting of: α-naphthyl, β-naphthyl, phenyl, 4-chlorophenyl, 2-chlorophenyl, 3,4-dichlorophenyl, 4-nitrophenyl, 4-fluorophenyl, 4-bromophenyl, 3-methoxyphenyl, 3-methylthiophenyl, 4-methylthiophenyl, 4-alkylphenyl in which the alkyl has from one to four carbon atoms, and 3-alkylphenyl in which the alkyl has from one to four carbon atoms;

$R_1$ is selected from the group consisting of hydrogen, a straight chain alkyl having from one to three carbon atoms, a halo-alkyl having from three to four carbon atoms, said halo being chloro or bromo; and $R_2$ is a halo-alkyl having from three to four carbon atoms, said halo being chloro or bromo.

2. The compound of claim 1, wherein $R_1$ is hydrogen.

3. The compound of claim 2, wherein $R_2$ is selected from the halo-alkyl group consisting of 2-bromopropyl, 2,3-dibromopropyl, 2,3-dichloropropyl, 2,3-dibromobutyl, 3,4-dibromobutyl, and 3-bromobutyl.

4. The compound of claim 2, wherein $R_2$ is 2,3-dibromopropyl.

5. S-phenyl N-2,3-dibromopropylthiolcarbamate.

6. S-4-nitrophenyl N-2,3-dibromopropylthiolcarbamate.

7. S-3,4-dichlorophenyl N-2,3-dibromopropylthiolcarbamate.

8. The compound of claim 1, wherein $R_1$ is a straight chain alkyl of from one to three carbon atoms.

9. The compound of claim 8, wherein $R_2$ is 2,3-dibromopropyl.

10. The compound of claim 1, wherein $R_1$ is methyl.

11. The compound of claim 10, wherein $R_2$ is 2,3-dibromopropyl.

12. The compound of claim 1, wherein $R_1$ and $R_2$ are straight chained halo-alkyls of from three to four carbon atoms.

13. The compound of claim 1, wherein both $R_1$ and $R_2$ are selected from 2,3-dibromopropyl, 2,3-dichloropropyl, 2-methyl-2,3-dibromopropyl, and 2-methyl-2,3-dichloropropyl.

14. The compound of claim 1, wherein both $R_1$ and $R_2$ are 2,3-dibromopropyl.

* * * * *